United States Patent [19]
Dozono

[11] Patent Number: 5,250,301
[45] Date of Patent: Oct. 5, 1993

[54] METHOD FOR TREATING DIGESTIVE ORGAN DISORDERS

[75] Inventor: Fumio Dozono, 3040, Ohaza-Homanbo, Takajo-cho, Kitamorokata-gun, Miyazaki-ken, Japan

[73] Assignees: Fumio Dozono, Miyazaki; Naohiko Sato, Tokyo, both of Japan

[21] Appl. No.: 827,130

[22] Filed: Jan. 28, 1992

[30] Foreign Application Priority Data

Aug. 1, 1991 [JP] Japan .................................. 3-193301

[51] Int. Cl.$^5$ ............................................. A61K 35/78
[52] U.S. Cl. .................................. 424/195.1; 514/867; 514/886; 514/892; 514/926; 514/927
[58] Field of Search ..................... 424/195.1; 514/926, 514/927, 867, 886, 892

[56] References Cited

FOREIGN PATENT DOCUMENTS 3-127959 5/1991 Japan .
3-151321 6/1991 Japan .
3-220109 9/1991 Japan .
4-66535 3/1992 Japan .

Primary Examiner—John W. Rollins
Attorney, Agent, or Firm—Jordan and Hamburg

[57] ABSTRACT

A liquid internal medicine contains only an extract from stems of natural Stevia plants. The medicine is particularly effective for curing disorders of the digestive organs. The medicine contains a liquid obtained by fermenting a concentrate of an extract from Stevia stems, and is administered to patients as is or after dilution. As the medicine contains only the natural component, it is free of any side effects when applied to patients.

4 Claims, No Drawings

METHOD FOR TREATING DIGESTIVE ORGAN DISORDERS

The present invention relates to a liquid internal medicine which is prepared from a raw material of an extract of Stevia stems, and to a method of preparing the same. More precisely, it relates to a liquid internal medicine which is obtained by fermenting an extract from Stevia stems and is especially effective to disorders of digestive organs, and also for a method of preparing such a liquid internal medicine.

BACKGROUND OF THE INVENTION

Use of a Stevia extract as a sweetening agent has been well-known prior to completion of the present invention.

The present inventor has participated in the study of extracts from Stevia for many years, and he has already developed various inventions and filed patent applications to claim them. For instance, there may be mentioned a method of ripening a concentrated liquid, extracted from Stevia leaves by a special method, to prepare a sweetener (Japanese Published Kokai No. 3-127959); a horticultural manure obtained by fermenting an extract from a mixture of leaves and Stevia stems and a method of preparing the same (Japanese Published Kokia No. 3-220109); a bath lotion obtained by fermenting an extract from Stevia stems and a method of preparing the same (Japanese Published Kokai No. 3-151321); and a remedy for skin diseases and blood circulation promoting agent, obtained by concentrating, fermenting and ripening an extract from completely ripened Stevia stems, and a method of preparing the same (Japanese Published Kokai No. 4-66535).

The present inventor further researched and developed the above-mentioned inventions whereupon he has found that a substance obtained by concentrating, fermenting and ripening a Stevia extract is useful as an external medicine, especially, for preventing and curing disorders of the digestive organs. On the basis of these findings, he has completed the present invention.

SUMMARY OF THE INVENTION

One object of the present invention is to provide a liquid internal medicine that is free from any synthetic chemicals or drugs, which contains only one natural component and has excellent pharmaceutical effectiveness. Another object of the present invention is to provide a method of preparing such a liquid internal medicine.

Specifically, there is provided, in accordance with the present invention, a liquid internal medicine, which contains a liquid obtained by ripening a fermented and concentrated liquid extract from the stems of Stevia as an active ingredient.

There is also provided, in accordance with the present invention, a method of preparing a liquid internal medicine, in which a liquid extract from the matured stems of Stevia plants is concentrated and fermented, and the resulting liquid is further ripened.

DESCRIPTION OF THE PREFERRED EMBODIMENTS

The most important technical characteristic of the present invention is the point of use of a product, obtained by concentrating, fermenting and further ripening a liquid extract from completely matured stems of Stevia plants, as an internal liquid medicine.

Through the present inventor's research, it has been found that Stevia stems contain microorganisms which are not in Stevia leaves, that a product obtained by drying and powdering the stems and boiling the powdered stems in water to give a concentrated liquid, followed by heating, fermenting and ripening the liquid, preferably in a closed tank, has an excellent blood circulation promoting function and an excellent pharmaceutical effect as an internal medicine.

The liquid internal medicine of the present invention may be administered to patients as a drink, whereby the blood circulation of the patients will be promoted and the disorders of their digestive organs may be cured. As the characteristic aspect of the present invention, the raw material for preparing the medicine is, as mentioned above, a liquid as obtained by concentrating, fermenting and ripening an extract from only the stems of Stevia so that the medicine has a potent curative effect on various disorders.

Another characteristic aspect of the present invention is to use completely matured stems of Stevia plants as raw material for the medicine.

Precisely, Stevia as referred to herein is a perennial plant of Compositae (Asteraceae), which is native to Paraguay and Brazil in South America and is called *Stevia Rebaudiana Bertoni*. Stevia seedlings or cuttings are planted from April to May. Seed seedlings of Stevia are harvested two or three times a year while the leaves thereof are young and weak.

However, the Stevia stems to be used in the present invention should not be from such young and weak plants, since the pharmaceutical potency of them would not yet be sufficient. Preferably, matured Stevia stems harvested only once a year from October to November are to be used in the present invention. The harvested Stevia plants are dried at about 70° to 80° C. for 24 hours; they are grouped into leaves, stems and branches; only the stems are powdered to a size of 15 $\mu$m or less, preferably from about 1 to 8 $\mu$m; and the resulting powder is boiled for extraction. Stevia leaves contain components of a sweetener but contain few components having any pharmaceutical effect such as the intended liquid internal medicine. Therefore, the leaves are not suitable for use in the present invention.

Concentration, fermentation and ripening of the thus harvested Stevia stems may be implemented as described in the example below.

(1) Six liters of water are poured into an iron or stainless-steel pot and heated to boiling. Then, the heat is stopped, and one kg of the above-mentioned mixed powder of dried and powdered Stevia stems is gradually added to the container with gentle stirring. Next, heating is restarted and the whole is boiled for about one hour with stirring.

(2) The boiled-down raw material is separated into a liquid and a residue with a squeezer. The thus obtained first liquid (3 to 4 liters) is stored in a tank (concentrating pot).

(3) Next, about 4 liters of water are added to the above-mentioned iron or stainless steel pot and heated, and heating is stopped when the water reaches a boil. Then, the above-mentioned first squeezed residue is added thereto, mixed, heated and boiled down for about one hour.

(4) The thus boiled-down raw material is again separated into a liquid and a residue with a squeezer. The thus obtained second liquid is about 3 liters.

(5) The second liquid is put in the tank (concentrating pot) containing the above-mentioned first liquid, mixed and boiled down for about 3 to 4 hours. After the concentrated liquid mixture has boiled-down to about one liter, the concentration process is finished. The sugar degree of the product after this process is from 20 to 25 degrees.

(6) The thus obtained concentrated liquid is filtered, put in a storage tank and fermented and ripened therein at a temperature of from 15° to 30° C., preferably from 15° to 25° C., for a period of time from 90 to 360 days, preferably from 180 to 360 days. Yeast is used for fermentation.

General analysis of the components constituting the ripened product was carried out by Nippon Foodstuff Sanitation Association, an authorized examination agency as designated by the Japan Welfare Minister, on the basis of the Japan Foodstuff Sanitation Law and the Drugs, Cosmetics and Medical Instruments Law. The results of Test No. 01-4651 and No. 01-6559 are as follows:

| | |
|---|---|
| Energy | 47 Kcal |
| Water | 84.2 g |
| Protein | 3.6 g |
| Lipid | 0.4 g |
| Carbohydrate (Saccharide) | 7.3 g |
| Ash | 4.5 g |
| Calcium | 120 mg |
| Iron | 1.3 mg |
| Sodium | 22 mg |
| Potassium (by atomic absorption metric method) | 2200 mg |
| Phosphorus (by molybdenum blue method) | 200 mg |
| Retinol | 0 |
| $\beta$-carotene | 23 $\mu$g |
| Vitamin A efficacy | 13 IU |
| Vitamin $B_1$ | 0 |
| Vitamin $B_2$ | 0.21 mg |
| Vitamin C (by high performance liquid chromatography) | 0 |
| Niacin (by microorganismic determination) | 2.4 mg |
| Arsenic (as $As_2O_3$) (by Gutzeit's method, with note of Sanitation Examination Method as edited by Nippon Pharmaceutical Association) Not detected (detection limit of the 0.1 ppm) | |
| Heavy Metal (as Pb) (Heavy Metal Test Method, by the Official Regulation of Food Additives, 5th Ed.) | Not higher than 10 ppm |

For concentration, a multi-stage concentration process comprising two or more concentration steps may be employed for more effective extraction of the active ingredient. However, the performance obtained through four or more concentration steps is not especially significant in view of the concentration of the final extract but is rather economically disadvantageous.

Where the liquid internal medicine of the present invention thus obtained is perorally administered, it may be diluted before use to a mixture from 1/5 to 1/50, preferably from 1/10 to 1/15, with water or a soft drink, in accordance with the condition of the patients.

Since the liquid internal medicine of the present invention is totally composed of a natural Stevia extract only, it is free from any harmful side effects when absorbed into the body. The internal medicine of the present invention has the effect of promoting blood circulation so that disorders of the digestive organs may be cured. Additionally, if the medicine is externally applied to the skin, the effect of treating skin disorders can be observed.

An acute toxicity test ($LD_{50}$) of the liquid internal medicine of the present invention was carried out by the Nippon Foodstuff Sanitation Association, an authorized examination agency as designated by the Japan Welfare Minister, on the basis of the Japan Foodstuff Sanitation Law and the Drugs, Cosmetics and Medical Instruments Law. The results of Test No. 01-4651-2 are as follows:

1. Object of Test: Acute toxicity test ($LD_{50}$)
2. Substance to be Tested: Concentrated Stevia liquid
3. Animals Used: Five-week old male ddy-line mice; three groups of ten mice each
4. Test Method:

Administration of test substance: Healthy mice were selected and no feed was given thereto for 18 hours. Then, a thick test liquid was perorally administered thereto with a Magensonde.

Amount administered: The test liquid was administered to each group having ten mice, in an amount respectively, of 1 ml/20 g, 0.75 ml/20 g and 0.5 ml/20 g.

Breeding condition: After administration of the test liquid (Day 0), the mice were bred under constant temperature and humidity for 7 days, while water and feed were added thereto freely.

5. Observation of Condition of the Mice During the Test: All mice in the first group, to which the maximum amount of 1 ml/20 g of the test liquid had been administered, displayed depression of spontaneous movement and depression of respiration for 30 minutes immediately after the administration of the test liquid, but all of them recovered to normal condition within 30 minutes thereafter.

The mice in the second group, to which 0.75 ml/20 g of the test liquid had been administered, showed slight depression of spontaneous movement immediately after the administration of the test liquid, but they recovered to normal condition within 20 minutes after administration of the same.

6. Test Result:

The weight of each mouse bred under the above-mentioned condition was measured every day, and their general condition was observed every day. During the test period, the weight of each mouse increased normally, and there was no special change found in any of the tested mice during the test period of 7 days.

From the above-mentioned results, the value of $LD_{50}$ of the concentrated Stevia liquid as tested above is 50 ml/kg or more, and the acute toxicity of the liquid is presumed to be extremely low.

The liquid internal medicine of the present invention was confirmed to have a pharmaceutical and medical effect on the following diseases.

Indications for the medicine of this invention are: Anorexia, indigestion, bloated feeling, acceleration of digestion, hyperacidity, upset stomach, feeling heaviness in stomach, nausea, disorders from overdrinking, gastralgia, diarrhea, loose passage, stomatitis, constipation, feeling cold, gastritis, gastric ulcer, and promotion of appetite.

The present invention will be explained in more detail by way of the following examples, which, however, are not intended to restrict the invention.

EXAMPLE 1

Matured Stevia plants were harvested at the beginning of November and were dried in a tobacco drier having an area of 6.6 m², at 75°+/−3° C. for 24 hours under the condition of an air flow rate of 30 m³/min.

Next, the plants were lightly beaten with a bar so as to separate them into stems, leaves, branches and impurities. Only stems were collected. The stems were cut with a cutter into small pieces of about 3 to 5 cm, then powdered twice with a Hitachi grinder and thereafter sieved to a fine powder having a mean particle size of 5 μm.

Next, 6 liters of water was poured into an iron pot and heated. After the water reached a boil, the heat was stopped. Then, 1 kg of the previously prepared fine powder of Stevia stems was gradually added to the pot with gentle stirring and was boiled down with stirring for one hour.

This was put into a Nishikawa squeezer and separated into a Stevia liquid and a residue. The thus obtained first liquid was about 4 liters, which was put in a tank (concentrating pot).

Next, 4 liters of water was put into the above-mentioned iron pot and heated. After the water reached a boil, the heat was stopped. The previously separated residue was gradually added to the pot and heating was again started. The whole was then boiled down for about 1 hour. This was put in the above-mentioned squeezer and separated into a Stevia liquid and a residue. The thus obtained second liquid was about 3 liters, and this was put in the above-mentioned tank (concentrating pot) containing the previous first liquid and the two were blended.

Next, the tank was heated and the content therein was boiled down. After about 4 hours, the concentrated liquid mixture was boiled down to about 1000 cc. The thus concentrated liquid was filtered through a cotton bag, and the resulting filtrate was put in a storage tank made of stainless-steel. This was then fermented and ripened therein at 25° C. for 360 days, whereupon the resulting liquid had a sugar degree of 21 degrees.

The liquid internal medicine thus obtained was a brownish-green liquid having a sweet aroma and an extremely low viscosity.

EXAMPLE 2

Examples of administration of the liquid internal medicine of the present invention are mentioned below.

| Sex | Age | Condition | Method of Peroral Administration | Results |
|---|---|---|---|---|
| Female | 37 | Constipation | 10 cc of 20% aqueous solution; once a day (in the morning) | She had a motion in two days, and her stool was regulated in 30 days. |
| Female | 63 | Anorexia | 2 cc of undiluted solution; once a day | Normal appetite was recovered in two days. |
| Female | 53 | feeling cold (serious case) | heated 50 cc of 1% aqueous solution; three times a day | The condition was eased in 9 days and cured in 15 days. |
| Male | 45 | upset stomach | 2 cc of undiluted solution; once a day | The condition was eased in 3 days and cured in 7 days. |

In accordance with the present invention, there is provided a liquid internal medicine containing only a fermented and concentrated liquid from an extract of Stevia stems, and the medicine has effective pharmaceutical activities for anorexia, indigestion, feeling of swollen stomach, acceleration of digestion, hyperacidity, bloated stomach, nausea, disorders from overdrinking, gastralgia, diarrhea, loose passage, stomatitis, constipation, feeling cold, abdominal pain, sore throat, gastritis, gastric ulcer, etc., as well as the effect of promoting blood circulation.

The medicine of the present invention can easily be prepared by powdering stems of Stevia, concentrating an extract from the powder by a multi-stage process, and fermenting and ripening the resulting concentrate.

While the invention has been described in detail and with reference to specific embodiments thereof, it will be apparent to one skilled in the art that various changes and modifications can be made therein without departing from the spirit and scope thereof.

What is claimed is:

1. A method for treating disorders of digestive organs, comprising perorally administering to a host afflicted with a disorder of a digestive organ, an effective amount of a liquid internal medicine comprising a fermented and concentrated extract from stems of matured *Stevia Rebaudiana Bertoni*.

2. A method as in claim 1, wherein said liquid internal medicine is an aqueous solution of said extract.

3. A method for preventing disorders of digestive organs, comprising perorally administering to a host susceptible to a disorder of a digestive organ, an effective amount of a liquid internal medicine comprising a fermented and concentrated extract from stems of matured *Stevia Rebaudiana Bertoni*.

4. A method as in claim 3, wherein said liquid internal medicine is an aqueous solution of said extract.

* * * * *